(12) United States Patent
Grozinger et al.

(10) Patent No.: US 6,255,481 B1
(45) Date of Patent: Jul. 3, 2001

(54) PHARMACEUTICAL SUSPENSION COMPRISING NEVIRAPINE HEMIHYDRATE

(75) Inventors: Karl G. Grozinger, Ridgefield; Amale A. Hawi, Danbury, both of CT (US)

(73) Assignee: Boehringer Ingelheim Pharmaceuticals, Inc., Ridgefield (*) Notice: Subject to any disclaimer, the term of this patent is extended or adjusted under 35 U.S.C. 154(b) by 0 days.

(21) Appl. No.: 09/517,564

(22) Filed: Mar. 2, 2000

Related U.S. Application Data

(63) Continuation of application No. 09/131,829, filed on Aug. 11, 1998.
(60) Provisional application No. 60/056,803, filed on Aug. 25, 1997.

(51) Int. Cl.[7] .......................... C07D 243/10; A61K 9/14; A61K 31/55
(52) U.S. Cl. .......................... 540/495; 424/489; 514/220
(58) Field of Search .......................... 514/220; 424/489; 540/495

(56) References Cited

U.S. PATENT DOCUMENTS 5,366,972 * 11/1994 Hargrave et al. .

OTHER PUBLICATIONS

Angel, et al; Proc. 50th Annual Meeting of the Electron Microscopy Society of America; pp. 1326–1327; 1992.

* cited by examiner

Primary Examiner—Thurman K. Page
Assistant Examiner—Amy E Pulliam
(74) Attorney, Agent, or Firm—Robert P. Raymond; Alan R. Stempel; Mary-Ellen M. Devlin

(57) ABSTRACT

An aqueous pharmaceutical suspension consisting essentially of nevirapine hemihydrate having a particle size between about 1 and 150 microns in diameter.

3 Claims, No Drawings

PHARMACEUTICAL SUSPENSION COMPRISING NEVIRAPINE HEMIHYDRATE

RELATED APPLICATIONS

This is a continuation of Ser. No. 09/131,829, filed Aug. 11, 1998, which is incorporated herein by reference. The benefit of prior provisional application Ser. No. 60/056,803, filed on Aug. 25, 1997, is hereby claimed.

BACKGROUND OF THE INVENTION (1) Field of the Invention

The invention relates to a novel composition of matter which is a pharmaceutical suspension comprising nevirapine hemihydrate.

(2) Description of the Related Art

Nevirapine, or 11-cyclopropyl-5,11-dihydro-4-methyl-6H-dipyrido[3,2-b:2',3'-e] [1,4] diazepin-6-one, is a known agent for the treatment of infection by HIV-1 (human immunodeficiency virus, type 1), which acts through specific inhibition of HIV-1 reverse transcriptase. Its synthesis and use are described in various publications including, inter alia, U.S. Pat. No. 5,366,972; European Patent Application No. 0 429 987, U.S. patent application Ser. No. 08/515,093 U.S. Pat. No. 5,571,912 and U.S. patent application Ser. No. 08/371,622 U.S. Pat. No. 5,569,760. Viramune® tablets, a pharmaceutical comprising nevirapine in tablet form, has recently been approved by the U.S. Food and Drug Administration for use in the treatment of HIV-1 infection.

Angel et al. [Proc. 50th Annual Meeting of the Electron Microscopy Society of America, pp. 1326–1327 (1992)] have disclosed that nevirapine exists as the hemihydrate stable form and as the anhydrous metastable form. This same reference describes an attempt to make an aqueous suspension of nevirapine, suitable for pediatric use, from the anhydrous form of the compound. The attempt was unsuccessful because, when formulated in aqueous suspension, the anhydrous nevirapine slowly converted to the hemihydrate form, yielding crystals of the hemihydrate which, over time, grew so large as to adversely affect drug dissolution and pharmaceutical performance.

SUMMARY OF THE INVENTION

The invention is an aqueous suspension of the hemihydrate form of nevirapine. It has been found, unexpectedly, that, when placed in aqueous suspension, the crystal size of the hemihydrate remains stable over time. For this reason, aqueous suspensions of nevirapine hemihydrate are pharmaceutically acceptable.

DETAILED DESCRIPTION OF THE INVENTION

Anhydrous nevirapine can be made by any of several known methods, including those described in the references mentioned above.

The hemihydrate is conveniently produced by recrystallization of the anhydrous material from an aqueous medium. This can be accomplished by treating an aqueous suspension of the anhydrous material, which is a free base, with a strong acid, such as HCl, to yield the acid addition salt. The salt is, in turn, treated with a strong base, such as NaOH, to yield the free base as a precipitate, in the hemihydrate form. The precipitate is removed from the aqueous medium by filtration, washed with water and dried until the water content is between about 3.1 and 3.9% by weight. Further drying, which would convert the hemihydrate to the anhydrous form is to be avoided. The term hemihydrate is intended to refer to nevirapine which contains about 0.5 mole of water.

For use in a pharmaceutically acceptable aqueous suspension, the particle size of the hemihydrate should be between about 1 and 150 microns in diameter. The hemihydrate produced as described above can be milled, if necessary, so that particle size will fall within this range.

A pharmaceutically acceptable aqueous suspension of nevirapine hemihydrate can be made by adding the hemihydrate to purified water, in ratios from 1 to 50 mg nevirapine hemihydrate to 1 mL of water, followed by agitation. The formulation can additionally comprise conventional pharmaceutical additives, such as, but not limited to, suspending agents and/or viscosity thickening agents such as, for example cellulose-based polymers or synthetic polymers, preferably cross-linked polymers such as the carbomers; wetting agents such as, for example, polyethylene oxides or polyoxyethylene sorbitan fatty acid esters (polysorbates); sweetening or flavoring agents, such as sucrose; and preservatives, such as, for example, the parabens.

By way of non-limiting description, a typical formulation in accordance with the invention would be one as described in the following table.

| Constituent | Range of Amount (g/100 mL) |
|---|---|
| Nevirapine Hemihydrate | 0.1–50 |
| Carbomer 934P, NF | 0.17–0.22 |
| Polysorbate 80, NF | 0.01–0.2 |
| Sorbitol Solution, USP | 5–30 |
| Sucrose, NF | 5–30 |
| Methylparaben, NF | 0.15–0.2 |
| Propylparaben, NF | 0.02–0.24 |
| Sodium Hydroxide, N.F.* | q.s. to pH 5.5–6.0 |
| Purified Water, USP | q.s. ad 100.0 mL |

*20% solution prepared

The invention is further illustrated by the following non-limiting examples.

EXAMPLE 1

Preparation of nevirapine hemihydrate

A glass lined reactor containing 318 Kg of nevirapine (anhydrous) is charged with 319 Kg of 37% HCl at a flow rate to maintain the internal temperature below 35° C. The mixture is agitated at 25–35° C. until all material is dissolved. The solution is filtered and diluted with 160 liters of purified water. The solution is neutralized with a 25% sodium hydroxide solution, while maintaining the temperature below 40° C. The resulting crystalline suspension is cooled to 15–20° C. for 30 minutes. The crystals are centrifuged and washed with purified water and dried at 30–40° C. The crystals are then dried under vacuum using a conventional vacuum tumble dryer for 8–24 hours, an air circulation tray dryer for 24–72 hours, or a Titus® centrifuge dryer (TZD) for 1 to 8 hours. The drug substance, which is the hemihydrate, is dried until the water content is between 3.1–3.9% as determined by a moisture balance on 100° C. for 30 min.

EXAMPLE 2

Preparation of Nevirapine Hemihydrate 26 g of nevirapine (anhydrous) are suspended in 100 mL of water. To the stirred mixture is added 30 mL of concentrated hydrochloric acid with cooling to maintain the temperature below 30° C. After 10 to 20 minutes, the colored solution is filtered and neutralized by the addition of 14.4 g sodium hydroxide in 50 mL of water. The resulting precipitate is filtered and washed with water. The wet crystalline material is transferred to trays and dried at 35–45° C. until a water content of 3.1 to 3.9% is obtained. The melting point of the resulting hemihydrate is 242–245° C. and analyzes for 3.1 to 3.6% of water, or about 0.5 mole of water.

EXAMPLE 3

Preparation of Aqueous 50 mg/5 ml Pharmaceutical Suspension of Nevirapine Hemihydrate
Composition

| Constituent | Amount (g/100 mL) |
| --- | --- |
| Nevirapine Hemihydrate | 1.035 |
| Carbomer 934P, NF | 0.2100 |
| Polysorbate 80, NF | 0.05000 |
| Sorbitol Solution, USP | 23.13 |
| Sucrose, NF | 15.00 |
| Methylparaben, NF | 0.1800 |
| Propylparaben, NF | 0.02400 |
| Sodium Hydroxide, N.F.* | q.s. to pH 5.5–6.0 |
| Purified Water, USP | q.s. ad 100.0 mL |

*20% solution prepared

Processing Method

A portion of purified water is heated to approximately 70° C. and the methylparaben and propylparaben are added while continuously mixing. Once the parabens have completely dissolved, the solution is allowed to cool to less than 35° C., and then the carbomer 934P is dispersed in the preservative solution while mixing. The pH is adjusted to pH 5.5–5.8 with 20% sodium hydroxide Solution. The gel is continually stirred for approximately 20 minutes and the pH remeasured. The sorbitol solution is added while mixing. Then the sucrose is added and mixing continued for 30 minutes. The polysorbate 80 is dissolved in a portion of purified water, the nevirapine is then added to the polysorbate 80 solution, and the mixture is homogenized for at least 40 minutes. The nevirapine/polysorbate 80 drug concentrate is thoroughly blended into the carbomer gel. The suspension is adjusted to volume or weight with purified water and blended for 30 minutes.

What is claimed is:

1. A method for preparing nevirapine hemihydrate which method comprises the steps of:

(a) treating an aqueous suspension of anhydrous nevirapine with a strong acid, to yield a solution of the acid addition salt;

(b) treating the solution of the acid addition salt produced in the previous step with a strong base, to yield the free base of nevirapine as a precipitate, in the hemihydrate form; and, (c) separating the precipitated nevirapine hemihydrate from the aqueous medium by filtration; and, (d) washing the precipitated nevirapine hemihydrate produced in the previous step with water.

2. The method for preparing nevirapine hemihydrate in accordance with claim 1, wherein the separated nevirapine hemihydrate produced in step (d) is dried until the water content is between about 3.1 and 3.9% by weight.

3. A method for preparing an aqueous suspension of nevirapine hemihydrate wherein the crystal size of the nevirapine hemihydrate is pharmaceutically acceptable and remains stable over time, which method comprises the steps of:

(a) treating an aqueous suspension of anhydrous nevirapine with a strong acid, to yield the acid addition salt;

(b) treating the acid addition salt produced in the previous step with a strong base, to yield the free base of nevirapine as a precipitate, in the hemihydrate form; and, (c) separating the precipitated nevirapine hemihydrate from the aqueous medium by filtration;

(d) washing the separated nevirapine hemihydrate with water;

(f) optionally milling the dried nevirapine hemihydrate to obtain a particle size that is suitable for producing a pharmaceutically acceptable suspension, if the particles are not already of such size; and, (g) mixing the dried and optionally milled nevirapine hemihydrate with water, to obtain the aqueous suspension.

* * * * *